United States Patent [19]

White

[11] Patent Number: 4,994,265

[45] Date of Patent: Feb. 19, 1991

[54] SHAVING COMPOSITION

[75] Inventor: Blanca A. White, Athens, Ga.

[73] Assignee: Aloe Scientific Labs, Chicago, Ill.

[21] Appl. No.: 40,431

[22] Filed: Apr. 20, 1987

Related U.S. Application Data

[63] Continuation-in-part of Ser. No. 773,432, Sep. 6, 1985, abandoned.

[51] Int. Cl.$^5$ ................. A61K 7/150; A61K 7/450
[52] U.S. Cl. ........................... 424/73; 424/74; 424/195.1; 514/783; 514/944
[58] Field of Search ............... 424/73, 74, 195.1; 514/783, 944

[56] References Cited

U.S. PATENT DOCUMENTS

| | | | |
|---|---|---|---|
| 2,965,109 | 12/1960 | Borzh | 132/289 |
| 3,541,581 | 11/1970 | Monson | 252/90 |
| 3,878,197 | 4/1975 | Maret | 424/195.1 |
| 3,892,853 | 7/1975 | Cobble | 424/195.1 |
| 4,465,629 | 8/1984 | Maughan | 424/195.1 |

FOREIGN PATENT DOCUMENTS

| | | | |
|---|---|---|---|
| 218441 | 4/1987 | European Pat. Off. | |
| 2143841 | 2/1985 | United Kingdom | 132/289 |
| 2167429 | 5/1986 | United Kingdom | 424/73 |

OTHER PUBLICATIONS

The CTFA Cosmetic Ingredient Dictionary, 3rd Edition (1982), pp. 9-10.
The CTFA Cosmetic Ingredient Dictionary, 3rd Edition, Supplement (1985), pp. 1-2.
Soap/Cosmetics/Chemical Specialties for Feb., 1977, pp. 34-38.
Soap/Cosmetics/Chemical Specialties for Mar., 1977, pp. 45-47.
Erde International (1983), pp. 40-44.
Drug and Cosmetic Industries, Jun. 1983, pp. 30 et seq.
Drug and Cosmetic Industries, Sep. 1985, pp. 42-46.
Drug and Cosmetic Industry, vol. 132, Jan. 1983, p. 39 et seq.
Drug and Cosmetic Industry, vol. 132, Jan. 1983, p. 40.
Drug and Cosmetic Industry, Feb. 1983, pp. 34-40.
Brochure, undated, National Aloe Science Council, "Approved Definitions for Aloe Vera".

*Primary Examiner*—Merrell C. Cashion, Jr.
*Assistant Examiner*—Susan S. Rucker
*Attorney, Agent, or Firm*—Neuman, Williams, Anderson & Olson

[57] ABSTRACT

A shaving composition comprising at least about 10 wt % aloe vera product, a cosmetically acceptable film forming agent, a cosmetically acceptable lubricity agent, and a cosmetically acceptable preservative. The shaving composition of the invention may be in the form of either a liquid or a gel. The composition can be used without prior application of water to the area to be shaved and can be packaged in a variety of forms which make it especially suitable for travelers, campers, and the like.

14 Claims, No Drawings

SHAVING COMPOSITION

CROSS REFERENCE TO RELATED APPLICATIONS

This application is a continuation-in-part of U.S. application Ser. No. 773,432, filed Sep. 6, 1985, now abandoned.

FIELD OF THE INVENTION

This invention relates to a shaving composition. More particularly this invention relates to a shaving composition which can be used without the prior application of supplemental water or soap.

BACKGROUND OF THE INVENTION

Since ancient times it has been known that shaving of human hair with a razor blade is greatly facilitated by the prior application of a suitable lubricant to the skin. Historically, these lubricants have comprised mixtures of water and a soap or surfactant which were agitated in a shaving cup to form a lather and applied with a shaving brush to the wetted surface to be shaved. The shaving cup and brush tended to be bulky and cumbersome, and the process of agitating the soap with water to form a lather often was untidy. In recent years manufacturers have sold foamable shaving lathers packaged in pressurized aerosol cans. These can dispense small amounts of a premixed composition of water and a soap or surfactant or in some cases a lather-forming water-containing gel. When applied to wetted skin, the compositions form a lather which provides a suitable lubricant for shaving. The pressurized cans, however, also have serious drawbacks. They tend to be bulky, which can be disadvantageous for travelers, campers, and the like. If the cans are subjected to extreme heat or high pressures they could explode, which can be not only a nuisance but dangerous. Thus, it is known that air travelers should not include aerosol cans in luggage which will be stored in an unpressurized airplane cargo compartment. Besides the problems with packaging, these compositions still require that the surface to be shaved be wetted before the shaving lubricant is applied. The necessity of proximity to a supplemental fresh water source while shaving can be a major inconvenience while traveling, camping, boating or the like. Shaving with lather and supplemental water can also be inconvenient and bothersome to bedridden patients in hospitals, nursing homes, and so forth.

SUMMARY OF THE INVENTION

It is thus one object of the invention to provide a shaving composition which does not require the prior application of supplemental water or soap to the area to be shaved before application of the composition.

It is another object of the invention to provide a shaving composition which is not lather-forming.

It is still another object of the invention to provide a shaving composition which can be packaged in a small, non-aerosol container such as a jar, squeeze bottle, collapsible tube, or the like, suitable for traveling, camping, and the like.

Other objects, advantages, and novel features of the invention will be set forth in part in the description which follows.

In one broad form, the present invention comprises a shaving composition comprising an aloe vera product having at least some of the beneficial active principles of the aloe vera plant, a film forming agent, a lubricity agent, and a cosmetically acceptable preservative. The aloe vera product is at least about 10% by weight of the composition. The composition is used without prior application of supplemental water to the area to be shaved, and is non-lathering. The composition may be in the form of a liquid or a viscous gel. The composition can be packaged in small, non-aerosol containers suitable for traveling, camping, or the like.

In a suitable shaving composition of the present invention in liquid form, the aloe vera product can be a commercially available aloe vera extract or aloe vera gel, the film forming agent can be a cosmetically acceptable high molecular weight polymer resin, and the lubricity agent can be a cosmetically acceptable hydroxy amide. An appropriate diluent can be used to obtain a composition of the desired concentration and consistency. Fragrance and a fragrance miscibility agent can also be used. When in the form of a viscous gel, the composition will also include a gelling agent and an alkaline neutralizing agent. The proportions of the aforementioned ingredients will depend on the particular ingredients used and the desired concentration, consistency and performance characteristics of the final composition.

The instant invention is a substantial improvement over the shaving compositions of the prior art. Users of the invention also obtain the known benefits of the active principles of the aloe vera plant included in the aloe vera product. The composition is also very convenient to use. It is used by simply applying a small amount to the area to be shaved, and shaving. It is not necessary to apply supplemental water to the skin before applying the composition, nor is it necessary to mix the composition with supplemental water or otherwise work the composition into a lather before applying. Furthermore, the composition does not contain any soap, so no soap residue will remain after shaving.

It may be seen that the present invention is especially suitable for those who wish to shave where fresh water for washing is not readily available, such as those traveling long distances by airplane, train, or ship or where preparation and cleanup with supplemental water would be inconvenient, such as for patients in a hospital bed. Furthermore, many applications may be packaged in a relatively small container, which is a major advantage for long distance travelers and for activities such as outdoor camping.

In liquid form the shaving composition of the instant invention may be packaged, for example, in plastic squeeze-type bottles or in roll-on type dispensers. In viscous gel form the shaving composition of the instant invention may be packaged, for example, in jars, in squeeze tubes, or in tear-open foil packets containing a single application. Containers of this type are not unduly sensitive to heat or external pressure, and thus are particularly convenient for travelers.

The shaving composition of the present invention is also amenable to packaging in the form of a shaving kit, the kit including a small container of the composition in either liquid or viscous gel form, and a razor which may or may not be disposable. Such kits could provide maximum convenience for users of the inventive composition.

DETAILED DESCRIPTION OF THE INVENTION

The instant invention is a shaving composition which may be in the form of a liquid or a viscous gel and which may be used without supplemental fresh water for lathering or rinsing. The composition contains at least about 10% by weight of an aloe vera product including beneficial active principles of the aloe vera plant. In some preferred formulations the composition may include at least 50% by weight of aloe vera product.

In the description of the invention which follows and in the claims, it is to be understood that all ingredients of the invention are intended to be limited to cosmetically acceptable ingredients such as could be safely applied to human skin, whether or not expressly stated as such. The word "gel" as used in the phrase "aloe vera gel" is intended here to denote a type of aloe vera product as in known in the art and as defined by *CTFA Cosmetic Ingredient Dictionary,* 3rd Ed., Supp., 1985, said definition being incorporated herein by reference, and is not to be confused with the phrase "viscous gel" which is intended here to denote the consistency of the composition of the invention in one of its embodiments. Thus the composition of the invention wherein the aloe vera product is aloe vera extract broadly has both liquid and viscous gel embodiments, and the composition of the invention wherein the aloe vera product is aloe vera gel also broadly has both liquid and viscous gel embodiments.

In liquid form, the invention may comprise
(a) at least about 10 wt% aloe vera product,
(b) about 5-20 wt % cosmetically acceptable film forming agent,
(c) about 1-20 wt % cosmetically acceptable lubricity agent, and
(d) about 0.2-1 wt % cosmetically acceptable preservative.

In some formulations, the liquid may also include
(e) about 0.05-0.2 wt % fragrance and
(f) about 0.15-0.6 wt % fragrance miscibility agent.

In a preferred embodiment of the invention in liquid form, such liquid may comprise:
(a) at least about 20 wt % aloe vera product,
(b) about 10-18 wt % cosmetically acceptable film forming agent,
(c) about 2-10 wt % cosmetically acceptable lubricity agent, and
(d) about 0.2-1 wt % cosmetically acceptable preservative.

In some preferred formulations, the liquid may also include:
(e) about 0.05-0.2 wt % fragrance and
(f) about 0.15-0.6 wt % fragrance miscibility agent.

In yet another embodiment, the composition of the invention in liquid form may comprise
(a) about 58-88 wt % aloe vera product,
(b) about 10-20 wt % cosmetically acceptable film forming agent,
(c) about 2-20 wt % cosmetically acceptable lubricity agent, and
(d) about 0.2-1 wt % cosmetically acceptable preservative.

The above embodiment may also include
(e) about 0.05-0.2 wt % fragrance, and
(f) about 0.15-0.6 wt % cosmetically acceptable fragrance miscibility agent.

In yet another version of the above embodiment, the inventive composition in liquid form may comprise
(a) about 60-78 wt % aloe vera product,
(b) about 12-18 wt % cosmetically acceptable film forming agent,
(c) about 10-20 wt % cosmetically acceptable lubricity agent, and
(d) about 0.3-0.8 wt % cosmetically acceptable preservative.

This version may also include
(e) about 0.05-0.2 wt % fragrance, and
(f) about 0.15-0.6 wt% cosmetically acceptable fragrance miscibility agent.

In some instances, it may be preferred to provide the shaving composition of the present invention in the form of a viscous gel.

In viscous gel form, the invention may comprise
(a) at least about 10 wt % aloe vera product,
(b) about 0.5-2 wt % cosmetically gelling agent,
(c) about 0.5-2 wt % cosmetically neutralizing agent,
(d) about 5-20 wt % cosmetically acceptable film forming agent,
(e) about 1-20 wt % cosmetically acceptable lubricity agent, and
(f) about 0.2-1 wt % cosmetically acceptable preservative.

In some formulations, the viscous gel may also include
(g) about 0.05-0.2 wt % fragrance, and
(h) about 0.15-0.6 wt % cosmetically acceptable fragrance miscibility agent.

In a preferred embodiment of the viscous gel shaving composition, said viscous gel may comprise
(a) at least about 20 wt % aloe vera product,
(b) about 0.5-2 wt % cosmetically acceptable gelling agent,
(c) about 0.5-2 wt % cosmetically acceptable neutralizing agent,
(d) about 10-18 wt % cosmetically acceptable film forming agent,
(e) about 2-10 wt % cosmetically acceptable lubricity agent, and
(f) about 0.2-1 wt % cosmetically acceptable preservative.

Said preferred formulations may also include
(g) about 0.05-0.2 wt % fragrance, and
(h) about 0.15-0.6 wt % cosmetically acceptable fragrance miscibility agent.

In yet another embodiment, the inventive composition in viscous gel form may comprise
(a) about 60-92 wt % aloe vera product,
(b) about 0.5-2 wt % cosmetically acceptable gelling agent,
(c) about 0.5-2 wt % cosmetically acceptable neutralizing agent,
(d) about 5-20 wt % cosmetically acceptable film forming agent,
(e) about 2-15 wt % cosmetically acceptable lubricity agent, and
(f) about 0.2-1 wt % cosmetically acceptable preservative.

The above embodiment may also include
(g) about 0.05-0.2 wt % fragrance, and
(h) about 0.15-0.6 wt % cosmetically acceptable fragrance miscibility agent.

In yet another version of the above embodiment, the inventive composition in viscous gel form may comprise (a) about 70-84 wt % aloe vera product,
(b) about 0.5-2 wt % cosmetically acceptable gelling agent,
(c) about 0.5-2 wt % cosmetically acceptable neutralizing agent,
(d) about 10-15 wt % cosmetically acceptable film forming agent,
(e) about 5-10 wt % cosmetically acceptable lubricity agent, and
(f) about 0.2-1 wt % cosmetically acceptable preservative.

This version may also include
(g) about 0.05-0.2 wt % fragrance, and
(h) about 0.15-0.6 wt % cosmetically acceptable fragrance miscibility agent.

In all of the above formulations, using either aloe vera extract or aloe vera gel as the aloe vera product ingredient, and where the final product is either in the liquid or gel form, it is to be understood that where the weight percentages given do not add up to 100%, the balance of the composition will substantially comprise more of the aloe vera product, or a cosmetically acceptable diluent such as water, or some combination of the aloe vera product and cosmetically acceptable diluent.

The use in a shaving composition of an aloe vera product having at least some of the beneficial active principles of the aloe vera plant is particularly advantageous. The beneficial properties of the active principles of the aloe vera plant have long been recognized. Thus, it is known to use aloe vera products in first-aid formulations for minor burns, cuts, scratches, insect bites and the like. Aloe vera products are also known for their ability to soothe skin rashes and other skin irritations. In the present invention, the healing and soothing properties of the active principles of the aloe vera plant are exploited, such that these beneficial properties are imparted to the shaving composition.

The use of aloe vera products has further advantages in the novel application of the present invention. The aloe vera products used are substantially clear, colorless, practically odorless and tasteless, all of which properties are highly regarded by consumers. The aloe vera products used are non-alkaline and have a pH similar to that of healthy skin, which aids in the prevention of contact dermatitis. The aloe vera products used have astringent properties which cause the pores of the skin to close, thus further protecting the skin from irritation during shaving. The aloe vera products also function as demulcents which soothe the skin. As many persons experience skin irritations and minor nicks during shaving, the presence of the beneficial properties of an aloe vera product in a shaving composition is especially desirable. The foregoing advantages accrue in varying degrees depending on the extent to which the active principles of the aloe vera plant are present in the particular aloe vera product used, and the concentration of the aloe vera product in the composition.

In one embodiment of the instant invention, the aloe vera product used can be aloe vera extract. Aloe extract is an extract of leaves of one or more species of *Aloe*, as defined in the *CTFA Cosmetic Ingredient Dictionary*, 3rd. Ed., 1982, p.10, incorporated herein by reference. An available commercial product suitable for use in the instant invention is a water based aloe vera extract sold by Terry Corporation, 3270 Pineda Avenue, Melbourne, Fla., 32935.

In another more preferred embodiment of the invention, the aloe vera product used can be aloe vera gel. Aloe vera gel is the mucilage obtained as the juice expressed from the leaves of *Aloe barbadensis Miller*. An available commercial product suitable for use in the instant invention is color stabilized aloe vera gel sold by Terry Corporation, 3270 Pineda Avenue, Melbourne, Fla., 32935.

The cosmetically acceptable film forming agent used in the composition of the invention acts to form a film which imparts slipperiness without tackiness to the area to be shaved. Certain cosmetically acceptable polymer resins having molecular weights between about 300,000-400,000 are known for this purpose. The resins cause the hair follicles to stand up, thereby facilitating the shaving process. It is known to use such polymer resins in compositions for the treatment of keratin-containing tissue such as nails and hair. Cosmetically acceptable high molecular weight polymer resins suitable for use with the instant invention include but are not limited to polyquaternium-11, a quaternary ammonium polymer formed by the reaction of dimethyl sulfate and a copolymer of vinyl pyrrolidone and dimethyl aminomethylmethacrylate, having a molecular weight of about 400,000, and sold under the name Gafquat 755 by GAF Corporation; polyvinylpyrrolidone, PVP, the linear polymer that consists of 1-vinyl-2-pyrrolidone monomers, having a molecular weight of about 360,000, and sold under the name PVP K-90 by GAF Corporation; and polyquaternium-10, a polymeric quaternary ammonium salt of hydroxyethyl cellulose reacted with a trimethyl ammonium substituted epoxate, having a molecular weight of about 400,000 and sold under the name UCARE Polymer LR 400 by Union Carbide Corporation. One skilled in the art of cosmetic compositions will recognize that other cosmetically acceptable film forming resins of similar composition and molecular weight can be used, such as those described in Grollier et al U.S. Pat. No. 4,240,450.

The cosmetically acceptable lubricity agent is used to impart lubricity to the product without greasiness. Lubricity agents suitable for use in the instant invention include cosmetically acceptable hydroxy amides. Hydroxy amides are also antiseptic, which is a particular advantage when used in a shaving composition, where the act of shaving could result in minor nicks and scratches. A hydroxy amide suitable for use in the present invention is Acetamide MEA, the aliphatic amide conforming to the formula

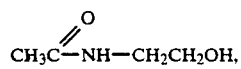

and also known as N-(2-hydroxyethyl)acetamide. One skilled in the art of cosmetic compositions will recognize that other cosmetically acceptable hydroxy amides may be used, for example, Lactamide MEA, the lactic acid analog of Acetamide MEA Both Acetamide MEA and Lactamide MEA are available from Croda Surfactants, Inc., 183 Madison Avenue, New York, N.Y., 10016.

A cosmetically acceptable preservative is necessary to ensure a suitably long shelf-life for the product. Suitably effective cosmetically acceptable preservatives include but are not limited to Quaternium 15, the quaternary ammonium salt that conforms to the formula

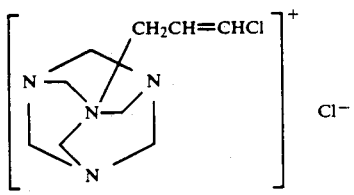

sold under the name Dowicil 20 by Dow Chemical U.S.A., Bennett Building, 2030 Dow Center, Midland, Mich., 48540; polymethoxy bicyclic oxazolidine, available from Nuodex, Inc., P.O. Box 365, Turner Place, Piscataway, N.J., 08854; and a mixture of diazolidinyl urea and parabens sold under the name Geraben II, and imidazolidinyl urea, sold under the name Germall 115, both available from Sutton Laboratories, Inc., 116 Summit Avenue, Chatham, N.J., 07928. It will be obvious to one skilled in the art that other cosmetically acceptable preservatives may be used.

In some formulations of the inventive composition, a small amount of fragrance will be deemed desirable. In such formulations, it will also be necessary to include a small quantity of a fragrance miscibility agent to promote homogeneous mixing of the fragrance throughout the product, as is known in the cosmetics art. A suitable fragrance miscibility agent is polysorbate 20, a mixture of laurate esters of sorbitol and sorbitol anhydrides, consisting predominantly of the monoester, condensed with approximately 20 moles of ethylene oxide, and sold under the name Tween 20 by ICI Americas Corp. It will be recognized by those skilled in the art that other cosmetically acceptable fragrance solubilizers may be used, such as Tween 40 and Tween 60, the palmitate and stearate analogs of Tween 20, and also available from ICI Americas Corp. Generally, the fragrance and fragrance miscibility agent should be provided in a ratio of about 1:3 on the basis of weight percent.

As has been noted, in some embodiments of the composition of the instant invention, a viscous gel consistency may be deemed more desirable than a liquid. A viscous gel consistency may be desired to accommodate user preference, or to facilitate the use of certain packaging means, such as squeeze tubes or tear-open foil packets. A viscous gel may be obtained by including in the formulation a gelling agent. Suitable gelling agents include the copolymers of acrylic acid and a polyallyl sucrose such as Carbomer 934, also known as Carbopol 934 and available from B.F. Goodrich Chemical Company. Carbopol 940 and 941, also available from B.F. Goodrich Chemical Company., are similar to Carbopoly 934. Copolymers of acrylic acid and polyallyl sucrose suitable for use in the composition of the invention and their method of preparation are generally described in U.S. Pat. No. 2,798,053 to Brown. Other cosmetically acceptable gelling agents suitable for use in the instant invention will be obvious to those skilled in the cosmetic arts.

Carbomer 934 and like copolymers can be considerably more acid than normal skin. It is therefore necessary to add to viscous gel formulations a slightly alkaline substance to partly neutralize the acid character of the gelling agent. An efficacious amount of the alkaline gel neutralizing agent will result in a formulation having a pH very close to that of normal skin. Cosmetically acceptable alkanolamines are suitable for this purpose, in particular triethanolamine, an organic amine of the formula $(HOCH_2CH_2)_3N$. Triethanolamine and Carbomer 934 may be added in a ratio of about 1:1 on a weight percent basis.

The method of preparing the inventive composition will vary depending on whether it is prepared in the form of a liquid or a viscous gel. The method of preparing the liquid comprises simply combining the aforelisted ingredients in the desired proportion by weight and mixing the ingredients at about 70° C. and at ambient pressure until a homogeneous mixture is obtained. The method of preparing the viscous gel comprises first combining the aloe vera product with an appropriate diluent such as water if desired. Gelling agent is then added, and mixed with heating to a temperature of about 70° C. until a homogeneous mixture is obtained. The temperature is decreased to allow the mixture to partially gel, and a portion of the gel neutralizing agent is added. The remaining ingredients are then added one at a time with mixing. If it is desired to add fragrance to the composition, the fragrance and fragrance miscibility agent can be first blended with a small amount of aloe vera product, then added to the mixture. Finally, as gelling continues the pH of the mixture can be adjusted with the remaining portion of the gel neutralizing agent. Advantageously, no extraordinary temperatures, pressures, or manufacturing equipment is required for the manufacture of the composition of the invention in either the gel or liquid form.

Yet another advantage of the present invention is that the various formulations are amenable to packaging in many different types of containers deemed desirable by consumers. In liquid form, the compositions may be packaged in a plastic squeeze-bottle; the user can squeeze a small amount of the composition onto the fingertips, and apply it to the area to be shaved. Similarly, the liquid may be packaged in a bottle having a non-aerosol pump, so that a small amount can be easily dispensed onto the fingertips. The liquid may also be packaged in a roll-on type bottle; the user can then conveniently and evenly apply an appropriate amount of the shaving composition over the surface to be shaved without getting the composition on the hands. In yet another alternative, a disposable paper towelette may be saturated with the liquid composition and enclosed in a tear-open foil packet. This packaging technique is known in the art as in the packaging of liquids suitable for cleaning ones' hands and face. This alternative is particularly advantageous for packaging an individual application of the liquid composition.

The viscous gel formulation of the inventive composition will be amenable to still other types of packaging. Relatively large quantities may be packaged in jars or in larger squeeze tubes. Smaller quantities, such as might be suitable for taking while traveling or camping, can be packaged in smaller squeeze tubes. Individual applications of the gel can be packaged in tear-open foil packets. If necessary, the viscous gel product can be diluted with up to about 20% additional water or other diluent for ease of packaging without detrimental effect on the product.

The inventive composition can also be packaged in the form of a kit, including a razor which may or may not be disposable, and a portion of the inventive composition packaged in any of the aforementioned forms. The kit may further include a small, soft, dry cloth for wiping the shaved area after shaving. The large number of applications available from a relatively small volume of the composition of the invention makes such a shaving kit ideal for traveling. Alternatively, when packaged with individual application portions of the inventive composition, such kits would make excellent complimentary items for overnight travelers by air or rail.

The following examples illustrate the inventive composition and methods for its preparation.

EXAMPLE I

The following ingredients are combined in a vessel:
(a) 80.00 grams of aloe vera extract procured from Terry Corporation of Melbourne, Fla.,
(b) 2.75 grams of Acetamide MEA
(c) 16.00 grams of Gafquat 755,
(d) 1.00 grams of Germaben II,
(e) 0.20 grams of Tween 20, and
(f) 0.05 grams of fragrance.

The ingredients are thoroughly mixed at about 70° C. and at ambient pressure for about 10 minutes until a homogeneous liquid is obtained. The liquid is packaged in plastic roll-on type bottles. The resulting product is considered an excellent shaving composition, with particular ease and convenience of application.

EXAMPLE II 1.7 kg of Carbopol 934 was slowly added to 131.21 kg of a 1:1 water solution of color stabilized aloe vera gel, available from Terry Corp. of Melbourne, Fla. with mixing and heating to about 70° C. Mixing was continued for about 2 hours until a homogeneous mixture was obtained. The temperature was decreased to allow partial gelling of the mixture. Triethanolmine in the amount of 0.852 kg was mixed into the partially gelled mixture. Then 4.69 kg Acetamide MEA, 27.26 kg Gafquat 755, and 1.7 kg Germaben II were added one at a time with thorough mixing after each addition. The Germaben II formed small white particles which dissolved with mixing and slight warmth. In a separate container were combined 0.341 kg Tween 20, 1.7 kg of the 1:1 water solution of aloe vera gel and 0.0852 kg fragrance. This mixture was mixed thoroughly into the gelled mixture. The composition was completed by slowly adding up to 0.852 kg triethanolamine to the mixture. The pH of the mixture was checked as the mixture thickened and the triethanolamine was added, so that the pH did not rise above 7.0, at which point the gel could liquefy. The procedure yielded 45 gallons (170.4 kg) of viscous gel product.

While particular embodiments of the invention, and the best mode contemplated by the inventor for carrying out the invention, have been shown, it will be understood, of course, that the invention is not limited thereto since modifications may be made by those skilled in the art, particularly in light of the foregoing teachings. For example, it will be understood that other cosmetically acceptable resins, hydroxy amides, preservatives, and fragrance miscibility agents may be available that may perform suitably in the inventive shaving composition. It is, therefore, contemplated by the appended claims to cover any such modifications as incorporate those features which constitute the essential features of these improvements within the true spirit and scope of the invention.

I claim:

1. A non-aqueous composition for use in shaving comprising at least about 10% by weight of an aloe vera extract or gel, from 0 to about 2% of a cosmetically acceptable a polyhydroxy or other gelling agent, from about 0.5 to about 2% by weight of a cosmetically acceptable neutralizing agent, from about 5 to about 20% by weight of a cosmetically acceptable film forming agent comprising polymers selected from the group of polyquaternium-11, polyvinyl pyrrolidone and polyquaternium-10, from about 1 to 20% by weight of a cosmetically acceptable lubricity agent selected from the group of hydroxyamide salts of acetic and lactic acids, and from 0.2 to 1% of a cosmetically acceptable preservative, said composition being in the form of a gel.

2. The composition of claim 1 wherein said aloe vera product comprises at least about 20% by weight of the composition.

3. The composition of claim 1, wherein said cosmetically acceptable film forming agent comprises about 10-18% by weight of the composition.

4. The composition of claim 3 wherein said cosmetically acceptable film forming agent is a polymer resin having a molecular weight between about 300,000-400,000.

5. The composition of claim 1, wherein said lubricity agent comprises about 2-10% by weight of the composition.

6. The composition of claim 1, wherein said lubricity agent is Acetamide MEA.

7. The composition of claim 1, wherein said preservative is selected from the group consisting of Quaternium-15, polymethoxy bicyclic oxazolidine, a mixture of diazolidinyl urea and parabens, and imidazolidinyl urea.

8. The composition of claim 1 wherein said gelling agent is about 0.5-2% by weight of the composition.

9. The composition of claim 1, wherein said alkaline neutralizing agent is an alkanolamine.

10. The composition of claim 9 wherein said alkaline neutralizing agent is triethanolamine.

11. A composition according to claim 1, in the form of a gel comprising at least about 10% by weight aloe vera gel, said composition being suitable for use in shaving.

12. A non-aqueous composition in the form a liquid comprising:
at least about 10 wt % aloe vera extract, about 5-20 wt % of a cosmetically acceptable polymeric film forming agent having a molecular weight of from 300,000 to 400,000; about 1-20 wt %, of a cosmetically acceptable hydroxy amide lubricity agent; and
about 0.2-1 wt % of a cosmetically acceptable preservative,
said composition being suitable for use in shaving.

13. The composition of claim 12 further comprising about 0.05-02 wt % fragrance, and about 0.15-0.6 wt % of a surfactant.

14. The composition of claim 12, wherein said cosmetically acceptable hydroxy amide is Acetamide MEA.

* * * * *

UNITED STATES PATENT AND TRADEMARK OFFICE
CERTIFICATE OF CORRECTION

PATENT NO. : 4,994,265

DATED : February 19, 1991

INVENTOR(S) : Blanca A. White

It is certified that error appears in the above-identified patent and that said Letters Patent is hereby corrected as shown below:

Column 10, line 45, after form and before a please insert --of--.

Signed and Sealed this

First Day of December, 1992

Attest:

DOUGLAS B. COMER

*Attesting Officer*  *Acting Commissioner of Patents and Trademarks*